United States Patent [19]

Komár Kalmár

[11] Patent Number: 4,459,262
[45] Date of Patent: Jul. 10, 1984

[54] ALLOYS BASED ON COBALT OR NICKEL, ESPECIALLY FOR PREPARING DENTAL PROSTHESES

[75] Inventor: József Komár Kalmár, Budapest, Hungary

[73] Assignee: Fogtechnikai Vallalat, Budapest, Hungary

[21] Appl. No.: 441,600

[22] PCT Filed: Mar. 3, 1982

[86] PCT No.: PCT/HU82/00008
§ 371 Date: Nov. 1, 1982
§ 102(e) Date: Nov. 1, 1982

[87] PCT Pub. No.: WO82/03007
PCT Pub. Date: Sep. 16, 1982

[30] Foreign Application Priority Data

Mar. 3, 1981 [HU] Hungary .............................. 526/81
Mar. 3, 1981 [HU] Hungary .............................. 527/81

[51] Int. Cl.³ .................... C22C 19/05; C22C 19/07
[52] U.S. Cl. .................................. 420/436; 420/442; 420/443; 433/207
[58] Field of Search ............... 420/436, 442, 443, 455; 433/207, 222

[56] References Cited

U.S. PATENT DOCUMENTS 4,053,308 10/1977 Tesk et al. ......................... 420/443
4,255,190 3/1981 Prosen ............................... 420/436

*Primary Examiner*—Rutledge, L. Dewayne
*Assistant Examiner*—Robert L. McDowell
*Attorney, Agent, or Firm*—Gabriel P. Katona

[57] ABSTRACT

A cobalt-or nickel-base alloy, which is especially suited for the preparation of dental prostheses, because it is sufficiently corrosion- and wear-resistant, cold-formable, and colorfast and has good castability, the possesses the strength properties of the noble metal alloys known from dental technology. The alloy contains in addition to the base metal 10–50% (wt.) chromium and 0.2–4.5% (wt.) gallium. The new alloys can additionally contain 0.05–0.08% (wt.) lanthanum, 0.03–0.1% (wt.) neodymium, and 1.0–6.0% (wt.) molybdenum.

Due to its elasticity and low density the alloy is particularly suited for firm, i.e. firmly anchored dental prostheses. However, it is also best suited for the production of base plates, anchoring clamps and clamping systems of removable dental prostheses.

Since the alloy does not contain any noble metal, the ingredients can be easily procured and the production costs are only a fraction of the costs of noble metal alloys.

4 Claims, No Drawings

ALLOYS BASED ON COBALT OR NICKEL, ESPECIALLY FOR PREPARING DENTAL PROSTHESES

FIELD OF THE INVENTION

The invention relates to an alloy based on cobalt or nickel, especially for the preparation of dental prostheses which are corrosion- and wear-resistant, can be formed in the cold state, polishable, true in colorfast and weldable.

STATE OF THE ART

Dental prostheses are known to be made in two different forms, those that are firmly attached to the available teeth, and those that are removably loosely inserted.

The firmly attached prostheses have been prepared in dentistry for several decades by a process involving one or more steps.

Dental technicians completed the crowns from pre-manufactured sockets made from corrosion-resistant steel according to the so called "pulling" method.

Bridges are prepared through soldering the crowns that are brought onto the supporting teeth in the above manner, with bridge bodies cast by separate modeling.

This technology incurs numerous problems and possibilities or error in the setting up and preparation of the width and the length of the crowns as well as in the soldering together of the crowns, and also in the soldering together of the crowns and the bridge bodies. The fit is, therefore, not always perfect and this affects the useful life of the supporting teeth. At the solder joints the bridge tends to become rigid and develop intercrystalline stress corrosion which leads to premature breaking. Furthermore, the preparation of a test crown is required which substantially increases the time required for the preparation of dental prosthetics, represents additional work for the dentist, and doubles the burden on the patient.

In the interest of better patient care recently the so called "single piece casting process" was developed for preparing crown- and bridge prostheses. In this case the entire prosthesis is prepared from a single casting cast from a single model.

In this case there are fewer possibilities of error, the edge closure of the crowns is more complete and since there is no need for separate trial bodies the prosthesis is completed more quickly, and the entire process requires less time from the dentist and the patient.

The number of dental prostheses prepared according to the "single piece casting process" shows a worldwide increasing tendency. In Hungary e.g. in the year 1979, compared to 1971, about hundred times as many dental prostheses were prepared according to the "single piece casting process". This corresponds still only to 37% of the total number of prostheses made in 1979, because the usefullness of the "single piece casting process" is limited due to strict requirements on the useful alloys as well as to the high price and availability problems occasioned thereby.

In the preparation of dental prostheses in accordance with the "single piece casting process" the alloy that is used should not only have sufficient strength, and resistance against wear and corrosion, but should also possess other properties, such as good casting ability, good ductility for accurate adjustment, polishability, colorfastness and elasticity. It should also assure a corresponding mechanical adhesion of plastic covering layers required for aesthetic reasons. The general strength requirements of suitable alloys are:

Tensile strength—min. 40 daN/mm$^2$,
Expansion—min. 10%,
Hardness—HV5/30 125–300.

These requirements are satisfied from among the available metal alloys used in dental technology, only by the noble metal alloys (gold-, silver-, platinum-, palladium alloys). These generally have the following characteristics:

Tensile strength—25–56 daN/mm$^2$,
Expansion—25–40%,
Hardness—HV5/30 125–200,
Density—16–19 g/cubic centimeter.

The cobalt-chromium alloys, such as Vitallium, that are mostly used for making bridge members, have the following properties:

Tensile strength—60–80 daN/mm$^2$,
Expansion—1–3%,
Hardness—HV5/30 300–500.

These alloys have only limited castability, because they are rigid and are too hard. Due to these latter properties small cross section prostheses made from these materials are very fragile and tend to splinter and tend to damage the adjacent healthy teeth during use. Therefore, they are not suitable for the preparation of dental prostheses cast from a single piece. Alloys for the preparation of removable dental fixtures have similar strength requirements and they have to have even better castability, ductility and elasticity. An alloy that is suitable for that purpose should have a castability which will completely fill casting forms for 0.3–0.4 mm thick base plates having relatively large surface with embedded anchoring clips. The cast plates and clips should resist the fatigue loads that occur during use; they should permit a snug adjustment in place with minimal permanent deformation. The alloys that are suited for that purpose should have a strength of at least 30 daN/square millimeter, expansion of at least 5% and a hardness of 140–450 HV5/30.

The requirements for manufacturing removable dental prostheses of required quality are satisfied also only by noble metals. The general characteristics of suitable noble metal alloys are:

Tensile strength—50–60 daN/mm$^2$,
Expansion—5–40%,
Hardness—140–350 HV5/30.
Density—16–19 g/cubic centimeter.

DISCLOSURE OF THE INVENTION

It is the object of the invention to provide a cobalt or nickel alloy, particularly for use in dentistry, which possesses the properties that are most important in dentistry, having the technical characteristics of the noble metal alloys that are at the present time the most important ones for dental prostheses. The alloy of the present invention enables the preparation of firmly placed dental prostheses and of base plates, clamps and clamping systems for removable dental prosthetics and contains no noble metals. Therefore, its cost of preparation represents only a fraction of the cost of preparing noble metal alloys, and its ingredients can be readily procured.

The above object of the invention can be accomplished with a cobalt- or nickel-base alloy which, in addition to the base metal also contains the additional main ingredients of 10-50% (wt.) chromium and 0.2-4.5% (wt.) gallium. Alloys of this type are resistant to wear and corrosion, ductile, polishable, colorfast and can be easily cast. The strength characteristics of these alloys satisfy the requirements of those that are required for use in the "single piece casting process," but its density is only half of that of the noble metal alloys and this presents a pronounced advantage in dental applications.

The advantageous properties of the alloy of the present invention can be further improved when it contains within the above limits (expressed as percent by weight) 13-20 chromium, 0.2-1.0 gallium, 0.05-0.08 lanthanum, 0.03-0.06 neodymium, and 0.3-0.6 silicon.

More suitably the properties of the alloy of the present invention can advantageously contain, in addition to the base metal, (expressed as percent by weight) 25-32 chromium, 0.4-1.2 gallium, 0.05-0.08 lanthanum, 0.03-0.06 neodymium and 0.3-1.6 silicon.

In another advantageous embodiment the alloy can contain, in addition to the base metal, 13-18% chromium, 0.4-1.0% gallium, 0.05-0.08% lanthanum, 0.03-0.06% neodymium and 1.0-2.0% molybdenum.

Other suitable embodiments of the invention include cobalt- or nickel-base alloys consisting essentially of the base metal and:
   15-20% (wt.) chromium, 0.2-0.6% (wt.) gallium, 0.05-0.08% (wt.) lanthanum, 0.03-0.06% (wt.) neodymium, and 0.3-0.6% (wt.) silicon; and
   13-18% (wt.) chromium, 0.4-0.8% (wt.) gallium, 0.05-0.08% (wt.) lanthanum, 0.03-0.06% (wt.) neodymium, and 1.0-5.0% (wt.) molybdenum.

Finally, it has been shown that embodiments of the alloy can contain, in addition to the base metal, 35-45% chromium, 0.2-1.0% gallium, 0.05-0.08% lanthanum, 0.03-0.06% neodymium, 1.5-5.5% molybdenum.

The alloys of the present invention have the following physical properties:
   Tensile strength—50-70 daN/mm$^2$,
   Expansion—10-40%,
   Contraction—10-30%,
   Hardness—150-400 HV5/30,
   Density—8-8.3 g/cubic centimeter,
   Liquidus temperature—1360-1380 degrees C.,
   Solidus temperature—1350 degrees C.

The alloy of the present invention has particularly good form-filling characteristics and castability: one can cast from this alloy 0.3-0.4 mm thick base plates and clamping systems (corresponding to a cross section of 0.07-0.09 square millimeter and a length of 10-25 mm). By way of comparison it should be mentioned here that known cobalt-chromium alloys will not fill casting molds for plates and clamps of less than 0.8-1.0 thickness.

The alloys of the present invention have very good corrosion resistance. They can be well polished and manifest an aesthetically durable gloss. They can be welded with the same materials and can be soldered with silver alloys, without a change in grain texture of the alloy.

The ductility (cold formability) of the material is good and enables any necessary correction of the metal frames of dental prostheses.

The noble oxide which forms on the metal frame of dental prostheses, especially gallium oxide, assures an especially good adhesion of aesthetic plastic coatings without affecting appearance of the prosthesis.

It is a further advantage of the alloys of the present invention that they contain no noble metals; therefore their cost of preparation is only 5-10% of the cost of preparing noble metal alloys of similar properties.

Especially advantageous is the comparison of the alloys of the present invention with noble metal alloys of reduced density. Therefore, the dental prostheses are lightweight and their preparation requires a lesser weight of alloy. For equal size prostheses one requires e.g. twice as much weight of noble metal alloy than from the alloys of the present invention.

One can reduce the material inventories by using the alloys of the present invention, because a dental technical laboratory does not have to maintain a large supply of prefabricated dental sockets in various sizes and shapes.

By the use of the alloys of the present invention the large increase of use of noble metal alloys in dentistry can be reduced, because the present alloys are well suited for use in the increasingly employed "single piece casting process".

PREFERRED EXAMPLES

In the following there are described by way of examples some advantageous compositions and embodiments of the alloys of the present invention, together with a brief explanation of the results. These examples are given by way of illustration and not of limitation.

EXAMPLE 1

Firmly placed dental prostheses (bridge-crown) were prepared from two different compositions of the alloy of the present invention. The alloys had the following compositions and properties:

| Composition | Amount "a" | Amount "b" | (% wt.) |
|---|---|---|---|
| Chromium | 16.1 | 30.3 | |
| Gallium | 0.31 | 0.98 | |
| Lanthanum | 0.07 | 0.06 | |
| Neodymium | 0.04 | 0.05 | |
| Nickel qs. to 100% | | | |
| Strength values | | | |
| Tensile strength | 65.7 | 68.5 | daN/mm$^2$ |
| Expansion | 41.7 | 39.6 | % |
| Hardness | 140 | 174 | HV5/30 |
| Contraction | 33.0 | 10.9 | % |

The finished dental prostheses were subjected to the usual clinical tests, however of twice the usual length. During the extended test period the dental prostheses did not show even the slightest damage and they fully satisfied the requirements.

EXAMPLE 2

Base plates, anchoring clamps and clamping systems of removable dental prosthese were prepared from two batches of the alloy of the present invention. The alloys that were employed had the following compositions and properties:

| Composition | Amount "a" | Amount "b" | (% wt.) |
|---|---|---|---|
| Chromium | 41.4 | 39.9 | |
| Gallium | 0.27 | 0.57 | |
| Lanthanum | 0.06 | 0.08 | |
| Neodymium | 0.04 | 0.05 | |
| Molybdenum | 4.96 | 2.10 | |
| Nickel qs. to 100% | | | |
| Strength values | | | |

| Composition | Amount "a" | Amount "b" | (% wt.) |
|---|---|---|---|
| Tensile strength | 67.8 | 74.1 | daN/mm² |
| Expansion | 37.4 | 31.5 | % |
| Hardness | 320 | 300 | HV5/30 |

The removable dental prostheses made from the two batches were observed, as explained in connection with Example 1, during a double length of the normally prescribed testing period. The base plates, anchoring clamps and clamping systems showed a good fit and experienced absolutely no damage during use. The dental prostheses completely satisfied the requirements.

EXAMPLE 3

Metal parts of various dental prostheses were cast from three batches of the alloys of the present invention. The alloys that were used had the following compositions and properties:

| Components | Batch 1 | Batch 2 | Batch 3 | (% wt.) |
|---|---|---|---|---|
| Chromium | 16.4 | 25.3 | 36.7 | |
| Gallium | 0.68 | 0.82 | 0.75 | |
| Silicon | 0.32 | 0.43 | 0.64 | |
| Manganese | 0.30 | 0.32 | 0.31 | |
| Molybdenum | 1.92 | — | 4.63 | |
| Cobalt qs. to 100% | | | | |

| Components | Batch 1 | Batch 2 | Batch 3 | (% wt.) |
|---|---|---|---|---|
| Strength values | | | | |
| Tensile strength | 50.2 | 58.1 | 63.4 | daN/mm² |
| Expansion | 14.3 | 12.9 | 7.6 | % |
| Hardness | 190 | 220 | 370 | HV5/30 |

Bridges and round bridges were made from Batch 1, bridges of larger length and telescope crowns were made from Batch 2, and plates were made from Batch 3. During clinical testing the finished dental prostheses did not show even the slightest damage and the parts completely satisfied all expectations.

I claim:

1. A cobalt- or nickel-base alloy consisting essentially of the base metal, 15–20% (wt.) chromium, 0.2–0.6% (wt.) gallium, 0.05–0.08% (wt.) lanthanum, 0.03–0.06% (wt.) neodymium, and 0.3–0.6% (wt.) silicon.

2. A cobalt- or nickel-base alloy consisting essentially of the base metal, 25–32% (wt.) chromium, 0.4–1.2% (wt.) gallium, 0.05–0.08% (wt.) lanthanum, 0.03–0.06% (wt.) neodymium, and 0.3–1.6% (wt.) silicon.

3. A cobalt- or nickel-base alloy consisting essentially of the base metal, 13–18% (wt.) chromium, 0.4–0.8% (wt.) gallium, 0.05–0.08% (wt.) lanthanum, 0.03–0.06% (wt.) neodynium, and 1.0–5.0% (wt.) molybdenum.

4. a cobalt- or nickel-base alloy consisting essentially of the base metal, 35–45% (wt.) chromium, 0.2–1.0% (wt.) gallium, 0.05–0.08% (wt.) lanthanum, 0.03–0.06% (wt.) neodymium, and 1.5–5.5% (wt.) molybdenum.

* * * * *